United States Patent [19]
Sabia et al.

[11] Patent Number: 5,811,482
[45] Date of Patent: Sep. 22, 1998

[54] NON-MIGRATING HYDROPHILIC SILICONE FINISH FOR HYDROPHOBIC SUBSTRATES SUCH AS NONWOVENS

[75] Inventors: Angelo J. Sabia, Yorktown Heights; Gerald J. Murphy, Hopewell Junction; Dorothy E. Parker, Mt. Kisco, all of N.Y.

[73] Assignee: OSi Specialties, Inc., Danbury, Conn.

[21] Appl. No.: 682,242

[22] Filed: Jul. 17, 1996

[51] Int. Cl.$^6$ .................................. C08K 5/06; B05D 5/00
[52] U.S. Cl. ............... 524/366; 210/500.21; 210/500.26; 210/500.27; 210/500.42; 427/245; 524/368
[58] Field of Search ........................ 427/245; 210/500.21, 210/500.26, 500.27, 500.42; 524/366, 368

[56] References Cited

U.S. PATENT DOCUMENTS 4,444,662 4/1984 Conover ................................ 210/500.2

*Primary Examiner*—John M. Cooney, Jr.
*Attorney, Agent, or Firm*—Scully, Scott, Murphy & Presser

[57] ABSTRACT

Disclosed are methods for increasing the ability of a porous hydrophobic substrate to transmit aqueous liquids by applying to a hydrophobic substrate selected polyether modified polydimethylsiloxanes. Further, disclosed are coated substrates prepared by the described methods.

16 Claims, 1 Drawing Sheet

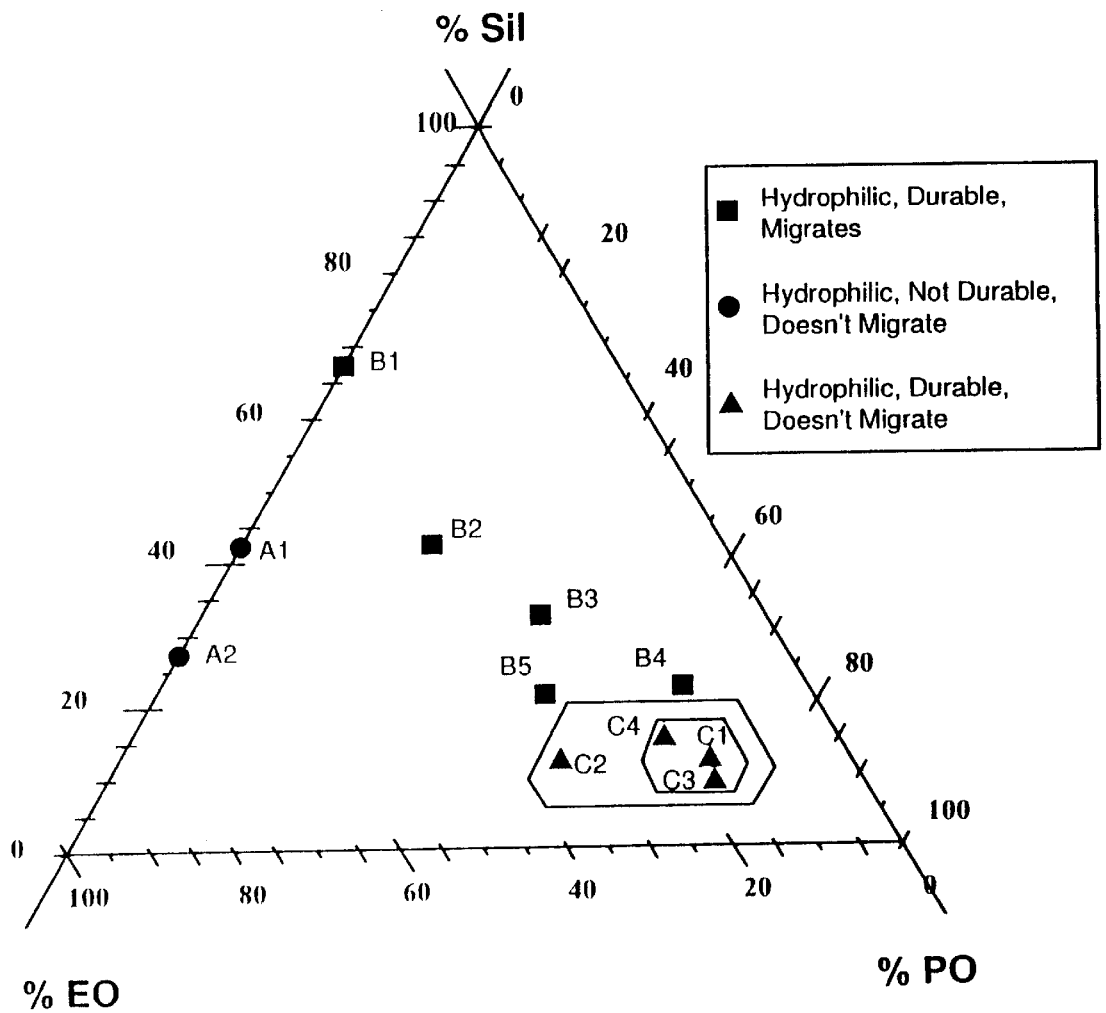

NON-MIGRATING HYDROPHILIC SILICONE FINISH FOR HYDROPHOBIC SUBSTRATES SUCH AS NONWOVENS

BACKGROUND OF THE INVENTION

Polyalkyleneoxide modified silicone copolymers are known, which can impart both hydrophilic and softening properties to hydrophobic nonwoven substrates such as polyester, polypropylene, polyethylene, glass and the like. Additionally, these polyalkyleneoxide modified silicone copolymers can also be applied to nonwoven substrates, such as rayon, cellulose, viscose and hemp, to enhance softening without adversely affecting their inherent hydrophilic attributes. These nonwoven substrates are utilized, for example, to fabricate diaper coverstock, garment and shoe interliners, adult incontinence products, tissues, filters, baby, surgical, and facial wipes, and the like. These silicone treatments can promote the wetting/absorption of urine, blood, fecal material, and other bodily fluids, while simultaneously softening the nonwoven substrate of these articles, making them easier to use and more pleasing to the touch.

It is desirable that these silicone treatments resist removal from the substrate by bodily fluids and remain functional through multiple uses, for example, when an infant wets a diaper several times while sleeping through the night. Concurrently, it is most desirable that hydrophilic silicone treatments remain where they were originally applied and not migrate to other areas within the article that are intended to remain hydrophobic. Such migration could promote undesired leakage around the waist and leg bands of a fabricated diaper, for example. This phenomenon could occur, for example, as a diaper is folded and stored for a time where the desired hydrophilically treated portion of the diaper comes in contact with a hydrophobic portion of the diaper.

Organic surfactants such as alkylphenol ethoxylates have also been used as hydrophilic finishes for synthetic nonwoven fabrics (e.g. the manufacture of diapers), but they are not durable to repeated contact with body fluids and do not provide sufficient softening properties. Heretofore, polyalkyleneoxide modified silicone copolymers containing primarily ethylene oxide moieties have been available that impart either, (A) excellent initial wetting with essentially no resistance to being washed off, or, (B) good initial wetting and excellent resistance to wash off, but with the aforementioned, undesirable tendency to migrate.

Examples of polyoxyethylene modified polydimethylsiloxane copolymers, which exhibit either type A or type B performance can be represented by the same general chemical structure, with different ranges for the values for x, y, and a, as shown below:

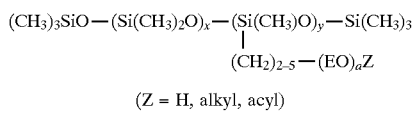

(Z = H, alkyl, acyl)

Examples of structures:

| Copolymer Type | x Range | y Range | a Range | Performance Deficiency |
|---|---|---|---|---|
| A | 12–20 | 5–6 | 7–8 | Limited Durability |
| B | 70–90 | 5–10 | 7–8 | Migrates |

Specific examples of polyethyleneoxide modified polydimethylsiloxane copolymers, which exhibit either type A or type B performance can be represented by this general chemical structure, with different values for the x, y, and m, and Z, as shown below. Both Copolymers A1 and B1 are derived from comparable polyethers and have similar degrees of substitution. The most pronounced difference in the structures of these two copolymers is in the number of dimethylsiloxy units (x=15 vs. 80). As a result, Copolymer A1 is completely soluble in water at all concentrations. In contrast, Copolymer B1 is only barely dispersible in water. When either of these copolymers is applied to a porous, hydrophobic substrate, such as a nonwoven polypropylene fabric, the treated surface is made readily hydrophilic. Upon repeated washings, however, the Copolymer A1 with its high water solubility is readily washed off, and the substrate gradually returns to being hydrophobic.

| Comparative Copolymers | x | y | a | Z | % Sil | % EO | Performance Deficiency |
|---|---|---|---|---|---|---|---|
| A1 | 15 | 5.5 | 7.5 | H | 42 | 58 | Limited Durability |
| B1 | 80 | 8.0 | 7.5 | Me | 67 | 33 | Migrates |

Copolymer B1 with its higher percent silicone (vide infra) and lower EO content is less susceptible to being rinsed off via this mechanism and imparts a more durable hydrophilic finish to the substrate. Such a trait is desirable, but the approach of using copolymers with high silicone contents has an unanticipated disadvantage. This is because the low surface energy of these copolymers makes them prone to migrate to any higher energy surface, which they might contact. This can occur, for example, in the construction of a disposable diaper, which may have some portions which are intended to be hydrophilic, such as the target area where urine is to be absorbed, and other areas, such as leggings and waistbands, that are intended to be hydrophobic to minimize or prevent unwanted leakage. If during folding or storage, the hydrophobic portion of such a diaper should contact the hydrophilically treated portion of the diaper, it is highly desirable that none of the hydrophilic finish migrate to the hydrophobic area. A notable deficiency of Copolymer B1, is that under the appropriate circumstances, it demonstrates this migration tendency.

BRIEF SUMMARY OF THE INVENTION

It has been discovered that a very limited range of certain organomodified silicones containing a relatively low silicone content, and relatively high propylene oxide level, as well as low ethylene oxide content provide adequate hydrophilicity, softening, and durability to being washed off by water or other aqueous liquids, such as bodily fluids, from porous hydrophobic substrates such as synthetic nonwovens without the aforementioned migration to abutting surfaces to which the organomodified silicone was not applied, as represented in the following Table 1.

TABLE 1

|  | Comparative Examples | | Product of Invention Polymer Type C |
|---|---|---|---|
|  | Polymer Type A | Polymer Type B |  |
| Readily Wettable | YES | YES | YES |
| Durable to Wash Off | NO | YES | YES |
| Resistant to Migration | YES | NO | YES |

The preferred compositions of this invention are polyether modified polydimethylsiloxanes of the formula (1):

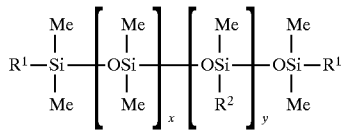

and mixtures thereof, where Me equals methyl, $R^1$ is methyl or $R^2$, and $R^2=C_pH_{2p}-(OC_2H_4)_m-(OC_3H_6)_n-OZ$, wherein x is about 0 to 200, y is about 0 to 50, p is about 2 to 5, preferably 3 to 4, m is about 3 to 30, preferably 3 to 15, n is about 3 to 60, preferably 6 to 30, and Z is independently in each occurrence hydrogen, an alkyl group with 1–4 carbons, or an acetyl group, preferably hydrogen.
with the proviso that when y=0, $R^1$ is an $R^2$ group, and that the values of x, y, m and n are selected such that the overall silicone content (% Sil) of the copolymer is between 5 and 20%, preferably between 8 and 16%, and the ethyleneoxy content of the copolymer is between 10 and 40%, preferably between 15 and 25%, and the propyleneoxy content is between 50 and 80%, preferably between 60 and 75%, with the additional restriction that the sum of % Sil and % EO and % PO must total 100%.

As used here and throughout this text, the silicone content or calculated percent silicone (% Sil) in a silicone-polyether copolymer is defined as the molecular weight of the total silicone backbone divided by the molecular weight of the whole copolymer. Similarly, the overall polyether content (% PE) in a silicone-polyether copolymer is defined as the molecular weight of each polyether pendant multiplied by the number of pendants divided by the molecular weight of the whole copolymer. If the pendant polyether is comprised of either only EO or only PO units, this % Polyether is equivalent to the % EO or % PO, respectively. If a pendant polyether contains both EO and PO units, then the overall % EO and % PO of the copolymer can be calculated by multiplying the % PE by the weight fraction of EO and weight fraction of PO in the polyether, respectively. Using this definition the sum of % Sil and % EO and % PO for any specific silicone-polyether copolymer must equal 100%.

BRIEF DESCRIPTION OF THE DRAWING

The FIGURE is a ternary diagram showing, in terms of % Sil, % EO and % PO, the compositions of products which do and do not exhibit the desired properties of the present invention.

DETAILED DESCRIPTION OF THE INVENTION

These polyalkylene oxide-modified polydimethylsiloxanes compositions are readily derived from a linear polydimethylsiloxane to which polyethers have been grafted through a platinum catalyzed hydrosilation reaction, as illustrated below for a model reaction between a methylhydrogen modified polydimethylsiloxane and an allyl polyethyleneoxide:

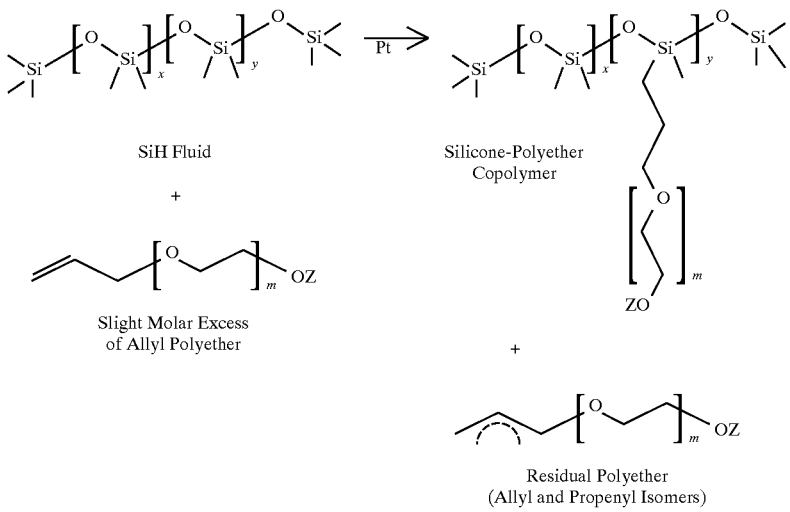

SiH Fluid

+

Slight Molar Excess of Allyl Polyether

Silicone-Polyether Copolymer

+

Residual Polyether (Allyl and Propenyl Isomers)

Any desired $R^2$ group can be grafted using a corresponding allyl reactant $CH_2=CH(CH_2)_{0-3}(OC_2H_4)_m-(OC_3H_6)_n-OZ$. The embodiments which are end-substituted with $R^2$ are made from the corresponding precursor endcapped with $-Si(CH_3)_2H$.

This process results in an alkyl-pendant copolymer, in which the polyalkyleneoxide groups are attached along the siloxane backbone through a series of, hydrolytically stable Si—C bonds. These copolymers have the following general formula:

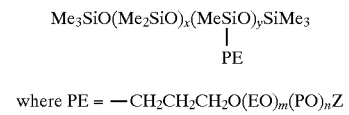

where PE = —$CH_2CH_2CH_2O(EO)_m(PO)_nZ$ where PE=—$CH_2CH_2CH_2O(EO)_m(PO)_nZ$

In this formula, Me represents methyl, EO represents ethyleneoxy, PO represents 1,2-propyleneoxy, where the EO and PO units may be either random or blocked, and Z can be either hydrogen or a lower alkyl group with 1 to 4 carbon atoms.

By varying the coefficients x, y, m and n, and the endblocking group, Z, a broad range of silicone-polyether copolymers have been developed. Several of these copolymers are sold by Witco Corporation, OSi Specialties Group, under the tradename Silwet® Surfactants.

The preferred silicone-polyether copolymers of this invention may be applied to the target substrate either alone or in mixtures, as neat materials, as aqueous solutions or dispersions, or after dilution with a suitable organic diluent, such as alcohols, alcohol ethoxylates, or fatty acid esters. Such preferred finishes may be applied using a variety of conventional techniques, including application by pad bath, spray, foam finishing, rotogravure printing, and the like, at overall concentrations of between 0.1% and 5.0%, preferably 0.2% to 2.0%, most preferably 0.5% to 1.0%, based on the dry weight of the substrate. Hydrophobic substrate compositions can include polypropylene, polyethylene, polyester, and glass. The form of the substrate can include nonwoven fabric, tissue, staple fibers, rock wool, thread, and the like. In its most preferred embodiment, the substrate is a nonwoven, polypropylene fabric.

The present invention is quite unexpected in that obtaining the desired performance represents not only a successful balance of Sil, PO and EO moieties in the molecule, but also represents the discovery that such a balance is even possible which achieves the desired combination of properties. This point is demonstrated in the following Table 2 and in the Figure appended hereto, which show that numerous products representing various combinations of Sil, PO and EO moieties provide unsatisfactory performance. Thus, the fact that any products at all exist which provide satisfactory performance is itself unexpected, as is the present discovery of products which in fact perform successfully as described herein.

Stated otherwise, it has heretofore been believed that the adjustments to the structure which would alleviate one of the performance deficiencies (susceptibility to being washed off; migration) would not alleviate the other deficiency, or would worsen it. Surprisingly, in the present invention both deficiencies are alleviated and avoided.

TABLE 2

| Comparative Copolymers | % Sil | % EO | % PO | Performance Deficiency |
|---|---|---|---|---|
| A1 | 42 | 58 | 0 | Not Durable |
| A2 | 27 | 73 | 0 | Not Durable |
| B1 | 67 | 33 | 0 | Migrates |
| B2 | 42 | 35 | 23 | Migrates |
| B3 | 32 | 27 | 41 | Migrates |

TABLE 2-continued

| Comparative Copolymers | % Sil | % EO | % PO | Performance Deficiency |
|---|---|---|---|---|
| B4 | 22 | 15 | 63 | Migrates |
| B5 | 21 | 32 | 47 | Migrates |
| Copolymers of invention | | | | |
| C1 | 12 | 17 | 71 | None |
| C2 | 12 | 35 | 53 | None |
| C3 | 9 | 18 | 73 | None |
| C4 | 15 | 21 | 64 | None |

(Product C4 is a 90/10 blend of products C1 and A1.)

The FIGURE is a ternary diagram showing the relative proportions of Sil, EO and PO in products of Formula (1) which were tested for their susceptibility to be washed off and to migrate. The area bounded by the hexagon ABCDEF represents the preferred proportions in the products used in the present invention. The hexagon GHIJKL bounds a particularly preferred group of products used in the present invention.

The present invention is further illustrated in the following description of tests in which product according to the invention, and other polyoxyalkylene-silicones, were subjected to protocols representative of the conditions to which commercial articles (such as disposable diapers) comprising treated hydrophobic substrates are exposed in use, and in storage. The data obtained in these tests demonstrate clearly that the present invention affords a superior and unexpected combination of properties not afforded by the reference products.

In the EDANA tests reported below, a low number signifies high retention of the silicone on the substrate. An increase of this number with successive insults (i.e., with successive applications of aqueous liquid), signifies progressive loss of the silicone from the substrate. Excessive loss is an undesirable phenomenon.

In the migration tests, a high number signifies high hydrophobicity which is desirable on the surfaces abutting the treated substrate. A loss of this hydrophobicity signifies migration of the silione to the abutting surface, which is undesirable.

The data reported in Tables I, II and III indicate that Polymer C1, which is within the present invention, exhibits the desirable combination of resistance to being washed off, and resistance to migration, whereas polymers outside the scope of the present invention did not exhibit this combination of properties.

Test Series I

TEST PROTOCOLS

100% Spunbonded Polypropylene Nonwoven
(1) Application

The silicone finishes were spray applied on one side of the nonwoven from aqueous dispersions such that 0.5 or 1.0 weight percent silicone solids resulted on the nonwoven coverstock (0.65 oz/yd$^2$) after air drying.

(2) Hydrophilicity

Two specific test procedures were used:

a) AATCC Method 79-1995 (Absorbency of Bleached Textiles)

b) EDANA Liquid Strike-Through Time (Method 150.3-96)

(3) Migration

Untreated 100% spunbonded SMS polypropylene webs (Spunbonded Meltblown Spunbonded) were placed beneath and above the 100% spunbonded polypropylene nonwoven web treated with silicone on one side only. A weight (0.5 lb/in$^2$) was placed on the nonwovens for 1 week at 50° C. to simulate storage and all layers evaluated for hydrophilicity. The desired result is to have the top and bottom layers remain hydrophobic and the silicone treated side to remain hydrophilic.

The nonwovens were stacked as follows:

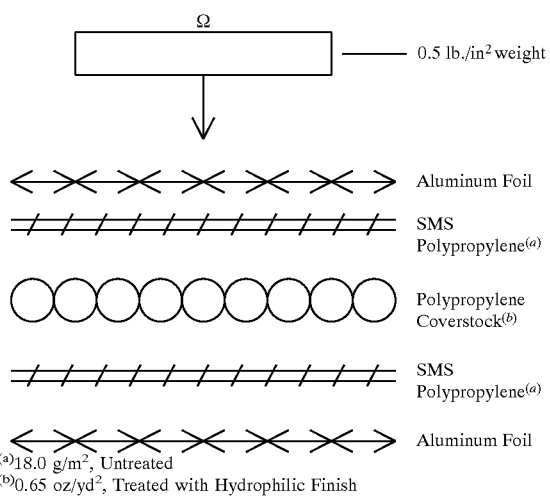

(a)18.0 g/m$^2$, Untreated
(b)0.65 oz/yd$^2$, Treated with Hydrophilic Finish (4) Durability The EDANA Liquid Strike-Through Time (150.3-96) was repeated 5 times on treated and the untreated 100% spun-bonded polypropylene nonwoven samples to simulate durability. Three hours elapsed time was allowed between insults.

Note: The aqueous media used for all the testing (hydrophilicity, migration, and durability) was a 0.9 weight percent sodium chloride solution.

Regarding the EDANA test, any value $\geq 5.0$ seconds is judged as being not durable.

TABLE I

Test Series I - Wetting Times in Seconds for 100% Spunbonded Polypropylene Nonwoven Using 0.9% NaCl Solution

|  | Untreated | Polymer A1 | | Polymer B1 | Polymer C1 | |
| --- | --- | --- | --- | --- | --- | --- |
|  | (As Rec'd) | 0.5%* | 1.0%* | 0.5%** | 0.5%* | 1.0%* |
| Initial Hydrophilicity Wetting Time (AATCC Test 79-1995) | >180*** | 2 | 1 | 1 | 30 | 12 |
| Durability to Repeated Washing EDANA Strike-through Time (Method 150.396) | | | | | | |
| 1 insult | >180 | 3.0 | 2.6 | 2.8 | 2.9 | 2.8 |
| 2 insults | >180 | 9.1 | 11.8 | 3.4 | 2.7 | 2.7 |
| 3 insults | >180 | 8.4 | 10.6 | 3.8 | 3.1 | 2.9 |
| 4 insults | >180 | 15.1 | 18.0 | 4.7 | 2.6 | 2.4 |
| 5 insults | >180 | 19.5 | 19.4 | 9.1 | 2.9 | 2.7 |
| Migration to Abutting Substrates After Aging Under Pressure for 5 days at 50° C. Wetting Time (AATCC Test 79-1995) | | | | | | |
| (SMS) Top Sheet (touches treated side) | >180 | >180 | 7.0 | 5.0 | >180 | >180 |
| Treated Nonwoven | >180 | 2.0 | 1.4 | 1.4 | 20 | 13 |
| (SMS) Bottom Sheet | >180 | >180 | 17 | 5.0. | >180 | >180 |

*Total Finish Level added to fabric on a weight basis
**Finish as applied included 15% w/w of an alkyl alcohol ethoxylate to disperse this water insoluble copolymer
***Test suspended after 180 seconds, >180 means the nonwoven did not wet, i.e., it was hydrophobic.

Test Series II

TEST PROTOCOLS

100% Extruded Polypropylene Filament Nonwoven (0.5 oz/yd$^2$)

(1) Application

The silicone finishes were spray applied from aqueous dispersions to one side of the nonwoven such that either 0.5 weight percent or 1.0 weight percent silicone solids resulted on the nonwoven after air drying.

(2) Hydrophilicity

Two specific test procedures were used:

a) AATCC Method 79-1995 (Absorbency of Bleached Textiles)

b) EDANA Liquid Strike-Through Time (Method 150.3-96)

(3) Migration

The nonwovens were stacked as follows:

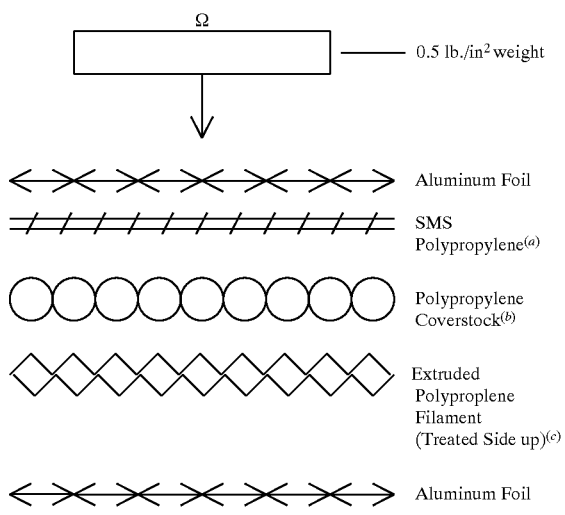

(a) 16.5 g/m²
(b) 18.0 g/m²
(c) 0.5 oz/y²

A weight (0.5 lb./in²) was placed on the nonwovens for up to 5 days @ 50° C. to simulate storage and all layers evaluated for hydrophilicity. Migration was noted when the initial hydrophobic Polypropylene Coverstock and the SMS Polypropylene became hydrophilic after contact with the Extruded Polypropylene Filament. The desired result is no migration of the hydrophilic finish, i.e., to have both the adjacent Polypropylene Coverstock and nearby SMS Polypropylene layers remain hydrophobic and the silicone treated side of the Extruded Polypropylene Filament to remain hydrophilic.

(4) Durability

The EDANA Liquid Strike-Through Test (Method 150.3-96) was repeated 5 times on the silicone treated, and untreated, control nonwoven samples to simulate durability. Three hours elapsed time between insults was used.

Note: The aqueous media used for all the testing (hydrophilicity, migration, and durability) was a 0.9 weight percent sodium chloride solution.

Regarding the EDANA test, any value $\geq 5.0$ seconds as judged as being not durable.

TABLE II

Test Series II - Wetting Times in Seconds for
100% Extruded Polypropylene Filament Nonwoven (0.5 oz/yd²) Using a 0.9% NaCl Solution

|  | As Rec'd | Polymer A1 | | Polymer B1 | | Polymer C1 Invention | |
|---|---|---|---|---|---|---|---|
| % Silicone solids Add-on | — | 0.5% | 1.0% | 0.5%* | 1.0%* | 0.5% | 1.0% |
| Initial Wettability (AATCC Test 79-1995) | >180* | 1 | 1 | 1 | 1 | 1 | 1 |
| Durability to Repeated Washing EDANA Strike-through Time (Method 150.396) | | | | | | | |
| 1 insult | 9.7 | 2.5 | 3.4 | 3.6 | 3.5 | 2.7 | 3.0 |
| 2 insults | 6.6 | 2.9 | 2.8 | 2.7 | 2.8 | 2.8 | 2.8 |
| 3 insults | 5.2 | 3.7 | 4.0 | 3.0 | 3.0 | 2.9 | 3.2 |
| 4 insults | 6.1 | 4.9 | 4.8 | 3.1 | 3.0 | 3.2 | 2.8 |
| 5 insults | 6.6 | 7.0 | 5.7 | 4.0 | 3.4 | 3.5 | 3.6 |
| Migration to Abutting Substrates After Aging Under Pressure for 5 days at 50° C. Wetting Time (AATCC Test 79-1995) | | | | | | | |
| SMS Polypropylene | >180 | >180 | >180 | 1 | 1 | >180 | >180 |
| Contact Angle, Degrees. (1 min./5 min.) | 115/115 | 115/112 | 115/115 | 0/0 | 0/0 | 111/111 | 115/114 |
| Polypropylene Nonwoven Coverstock*** | >180 | 1 | 1 | 1 | 1 | >180 | >180 |
| Extruded Polypropylene Filament Nonwoven | — | 1 | 1 | 1 | 1 | 1 | 1 |

*Total Finish Level added to fabric on a weight basis
**Finish as applied included 15% w/w of an alkyl alcohol ethoxylate to disperse this water insoluble copolymer
***Test suspended after 180 seconds, >180 means the nonwoven did not wet, i.e., it was hydrophobic.

TABLE III

Test Series I - Wetting Times in Seconds for
100% Spunbonded Polypropylene Nonwoven Using 0.9% NaCl Solution

|  | Untreated | Comparative Copolymers | | | | | | | Copolymers of Invention | | | |
|---|---|---|---|---|---|---|---|---|---|---|---|---|
|  |  | A1 | A2 | B1 | B2 | B3 | B4 | B5 | C1 | C2 | C3 | C4 |
| Initial Hydrophilicity Wetting Time (AATCC Test 79-1995) | >180 | $\leq 1$ | 1.4 | $\leq 1$ | $\leq 1$ | $\leq 1$ | 1.6 | 1.4 | 12 | 1.4 | 2.2 | 8 |
| Durability to Repeated Washing EDANA Strike-through Time | | | | | | | | | | | | |

TABLE III-continued

Test Series I - Wetting Times in Seconds for
100% Spunbonded Polypropylene Nonwoven Using 0.9% NaCl Solution

| | | Comparative Copolymers | | | | | | | Copolymers of Invention | | | |
|---|---|---|---|---|---|---|---|---|---|---|---|---|
| | Untreated | A1 | A2 | B1 | B2 | B3 | B4 | B5 | C1 | C2 | C3 | C4 |
| (Method 150.396) | | | | | | | | | | | | |
| 1 insult | 25 | 2.6 | 3.6 | 3.9 | 3.7 | 3.4 | 3.8 | 4.1 | 2.8 | 4.0 | 3.9 | 3.8 |
| 2 insults | 21 | 11.8 | 7.9 | 3.7 | 4.2 | 3.9 | 3.9 | 4.1 | 2.7 | 7.0 | 3.9 | 3.5 |
| 3 insults | 41 | 10.6 | 7.0 | 3.5 | 17 | 3.7 | 3.5 | 7.3 | 2.9 | 12 | 3.3 | 4.0 |
| 4 insults | 10 | 18.0 | 8.3 | 4.0 | 8.9 | 4.7 | 3.3 | 6.1 | 2.4 | 6.9 | 3.6 | 4.2 |
| 5 insults | 19 | 19.4 | 10.7 | 4.1 | 35 | 11 | 3.6 | 9.7 | 2.7 | 7.6 | 3.5 | 4.9 |
| Migration to Abutting Substrates After Aging Under Pressure for 5 days at 50° C. Wetting Time (AATCC Test 79-1995) | | | | | | | | | | | | |
| Top Sheet | >180 | 7.0 | >180 | ≦1 | 3.6 | 1.8 | 34 | ≦1 | >180 | >180 | >180 | >180 |
| Treated Nonwoven | >180 | 1.4 | 8.2 | ≦1 | ≦1 | 1 | 11 | ≦1 | 13 | 2.8 | 17 | 6 |
| Bottom Sheet | >180 | 17 | >180 | ≦1 | 6.2 | 1.8 | 44 | ≦1 | >180 | >180 | >180 | >180 |

*Total Finish Level added to fabric on a weight basis
**Finish as applied included 15% w/w of an alkyl alcohol ethoxylate to disperse this water insoluble copolymer
***Test suspended after 180 seconds, >180 means the nonwoven did not wet, i.e., it was hydrophobic.

We claim:

1. A method of increasing the ability of a porous hydrophobic substrate to transmit aqueous liquid therethrough, comprising applying to said substrate a coating selected from the group consisting of polyether modified polydimethylsiloxanes of the formula:

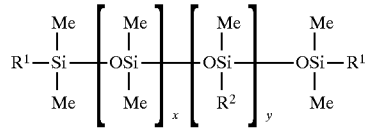

and mixtures thereof, where Me is methyl, $R^1$ is methyl or an $R^2$ group, and $R^2 = C_pH_{2p}$—$(OC_2H_4)_m$—$(OC_3H_6)_n$—OZ, wherein x is about 0 to 200, y is about 0 to 50, p is about 2 to 5, m is about 3 to 30, n is about 3 to 60, and Z is independently in each occurrence hydrogen, an alkyl group with 1–4 carbons, or an acetyl group, with the proviso that when y=0, $R^1$ is an $R^2$ group, and that the values of x, y, n and m are selected such that the overall silicone content of the copolymer is between 5 and 20% and the ethyleneoxy content of the copolymer is between 10 and 40% and the propyleneoxy content of the copolymer is between 50 and 80%.

2. A method according to claim 1 wherein p is 3–4.
3. A method according to claim 1 wherein m is 3–15.
4. A method according to claim 1 wherein n is 6–30.
5. A method according to claim 1 wherein the overall silicone content of the copolymer is between 8 and 16%.
6. A method according to claim 1 wherein the ethyleneoxy content of the copolymer is between 15 and 25%.
7. A method according to claim 1 wherein the propyleneoxy content of the copolymer is between 60 and 75%.
8. A method according to claim 1 wherein the substrate is nonwoven polypropylene.
9. A coated product which permits the transmission therethrough of aqueous liquid, said product comprising a substrate of porous hydrophobic material to which has been applied a coating selected from the group consisting of compounds of the formula

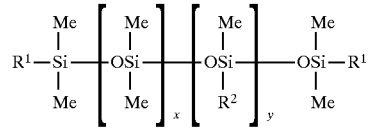

and mixtures thereof, where Me is methyl, $R^1$ is methyl or an $R^2$ group, and $R^2 = C_pH_{2p}$—$(OC_2H_4)_m$—$(OC_3H_6)_n$—OZ, wherein x is about 0 to 200, y is about 0 to 50, p is about 2 to 5, m is about 3 to 30, n is about 3 to 60, and Z is independently in each occurrence hydrogen, an alkyl group with 1–4 carbons, or an acetyl group, with the proviso that when y=0, $R^1$ is an $R^2$ group, and that the values of x, y, n and m are selected such that the overall silicone content of the copolymer is between 5 and 20% and the ethyleneoxy content of the copolymer is between 10 and 40% and the propyleneoxy content of the copolymer is between 50 and 80%.

10. A product according to claim 9 wherein p is 3–4.
11. A product according to claim 9 wherein m is 3–15.
12. A product according to claim 9 wherein n is 6–30.
13. A product according to claim 9 wherein the overall silicone content of the copolymer is between 8 and 16%.
14. A product according to claim 9 wherein the ethyleneoxy content of the copolymer is between 15 and 25%.
15. A product according to claim 9 wherein the propyleneoxy content of the copolymer is between 60 and 75%.
16. A product according to claim 9 wherein the substrate is nonwoven polypropylene.

* * * * *

UNITED STATES PATENT AND TRADEMARK OFFICE
CERTIFICATE OF CORRRECTION

PATENT NO. : 5,811,482  
DATED : Sept. 22, 1998  
INVENTOR(S) : Angelo J. Sabia, et al.

Page 1 of 2

It is certified that error appears in the above-identified patent and that said Letters Patent is hereby corrected as shown below:

On the title page, under item [56] References Cited, add the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 0 | 5 | 9 | 8 | 2 | 04 | A1 | 05/25/94 | European | | | | |
| | DE | 3 | 8 | 02 | 62 | 2 | | A1 | 08/10/89 | Germany | | | | |
| | | 0 | 6 | 6 | 9 | 4 | 20 | A2 | 08/30/95 | European | | | | |
| | | 0 | 6 | 0 | 7 | 7 | 96 | A1 | 07/27/94 | European | | | | |
| | | 0 | 3 | 7 | 2 | 8 | 9 | 0 | 06/13/90 | European | | | | |
| | | 0 | 4 | 10 | 4 | 8 | 5 | A1 | 01/30/91 | European | | | | |

UNITED STATES PATENT AND TRADEMARK OFFICE
CERTIFICATE OF CORRRECTION

PATENT NO. : 5,811,482
DATED : Sept. 22, 1998
INVENTOR(S) : Angelo J. Sabia, et al It is certified that error appears in the above-identified patent and that said Letters Patent is hereby corrected as shown below:

OTHER DOCUMENTS

| | | |
|---|---|---|
| | European Search Report in European Appln. No. EP 97113014 corresponding to | |
| | U. S. S. N. 08/682,242. (12/97) | |
| | | |

Signed and Sealed this

Thirteenth Day of April, 1999

*Attest:*

Q. TODD DICKINSON

*Attesting Officer*   *Acting Commissioner of Patents and Trademarks*